United States Patent
Tsai et al.

(10) Patent No.: US 10,159,459 B2
(45) Date of Patent: Dec. 25, 2018

(54) MULTI-MIC SOUND COLLECTOR AND SYSTEM AND METHOD FOR SOUND LOCALIZATION

(71) Applicant: iMEDI PLUS Inc., Zhubei, Hsinchu (TW)

(72) Inventors: Kun-Hsi Tsai, Zhubei (TW); Sheng-Hsiang Kung, Miaoli (TW); Shih-Cheng Lan, Taipei (TW); Yun-Fan Chang, New Taipei (TW)

(73) Assignee: iMEDI PLUS Inc., Zhubei (TW)

( * ) Notice: Subject to any disclaimer, the term of this patent is extended or adjusted under 35 U.S.C. 154(b) by 0 days.

(21) Appl. No.: 15/808,901

(22) Filed: Nov. 10, 2017

(65) Prior Publication Data
US 2018/0132815 A1 May 17, 2018

Related U.S. Application Data

(60) Provisional application No. 62/420,573, filed on Nov. 11, 2016.

(51) Int. Cl.
| | |
|---|---|
| *A61B 7/04* | (2006.01) |
| *A61B 7/02* | (2006.01) |
| *H04R 1/46* | (2006.01) |
| *G10L 21/10* | (2013.01) |
| *A61B 5/00* | (2006.01) |
| *G01H 3/00* | (2006.01) |
| *G01S 5/18* | (2006.01) |
| *G10L 25/66* | (2013.01) |
| *H04R 29/00* | (2006.01) |
| *G10L 21/0216* | (2013.01) |

(52) U.S. Cl.
CPC .............. *A61B 7/04* (2013.01); *A61B 5/0004* (2013.01); *A61B 7/026* (2013.01); *G01H 3/00* (2013.01); *G01S 5/18* (2013.01); *G10L 21/10* (2013.01); *G10L 25/66* (2013.01); *H04R 1/46* (2013.01); *H04R 29/006* (2013.01); *G10L 2021/02166* (2013.01)

(58) Field of Classification Search
CPC ....................................................... A61B 7/04
See application file for complete search history.

(56) References Cited

U.S. PATENT DOCUMENTS

| | | | |
|---|---|---|---|
| 6,790,183 B2 * | 9/2004 | Murphy ................ | A61B 5/061 600/532 |
| 8,475,396 B2 * | 7/2013 | Jones .................... | A61B 7/026 600/586 |

(Continued)

*Primary Examiner* — Olisa Anwah
(74) *Attorney, Agent, or Firm* — Chieh-Mei Wang

(57) ABSTRACT

A sound localization system includes a multi-mic sound collector and a computing device. The multi-mic sound collector includes a carrier and a plurality of sound receivers removably attached to the sound receivers. The computing device includes a data communicator, a synchronizer, and a processor. The data communicator receives preprocessed audio data from the multi-mic sound collector. The synchronizer synchronizes the preprocessed audio data. The processor analyzes the synchronized audio data to identify and localize a target audio feature. A sound localization method of the sound localization system is also provided. The present invention facilitates monitoring of the functioning or physiological signs of a monitored subject and allows early detection and diagnosis of abnormalities or diseases.

18 Claims, 12 Drawing Sheets

(56) References Cited

U.S. PATENT DOCUMENTS

| | | |
|---|---|---|
| 8,701,491 B2 | 4/2014 | Scholte et al. |
| 9,526,419 B2 * | 12/2016 | Derchak .............. A61B 5/0002 |
| 2014/0300490 A1 * | 10/2014 | Kotz ................... A61B 5/0028 |
| | | 340/870.3 |
| 2016/0050984 A1 * | 2/2016 | Ward .................. G01N 1/2273 |
| | | 2/102 |
| 2016/0354053 A1 * | 12/2016 | Tsai .................... A61B 5/7246 |
| 2017/0258390 A1 * | 9/2017 | Howard .................. A61B 5/16 |

* cited by examiner

MULTI-MIC SOUND COLLECTOR AND SYSTEM AND METHOD FOR SOUND LOCALIZATION

CROSS-REFERENCE TO RELATED APPLICATION

The present disclosure claims the benefit of U.S. Provisional Application No. 64/420,573, filed on Nov. 11, 2016.

FIELD OF THE INVENTION

The present disclosure relates generally to a system and method for sound localization, and more particularly to a multi-mic sound collector and a system and method for precise localization of abnormal sounds.

BACKGROUND OF THE INVENTION

Functioning of a subject can be assessed by analysis of the sounds coming from inside of the subject. For example, abnormal sounds made by an operating machine could be an indicator for malfunction of the components of the machine. Similar in medical and healthcare fields, auscultation of the sounds caused by movements of various organs of the body has been a common tool for diagnosis of the health conditions of a live subject.

Conventional sound analysis samples sounds at one spot at a time and requires professionals that have been specifically trained to identify abnormal sounds from regular ones and environmental noise. However, single spot detection often results in limited and sometimes misleading information. For example, as pathological breathing sound feature varies by symptoms and spots of auscultation, conventional single spot auscultation has not been a useful tool for diagnosis of asthma.

Furthermore, although the emergence of electronic sound analyzers has facilitated the sound analysis process, precise localization of the source of abnormal sounds has remained a challenge.

BRIEF SUMMARY OF THE INVENTION

An embodiment of the present invention provides a sound localization system. The sound localization system includes a multi-mic sound collector and a computing device. The multi-mic sound collector includes a plurality of sound receivers for collecting sound data of a subject. The computing device is in communication with the multi-mic sound collector, and includes a data communicator for receiving preprocessed audio data from the multi-mic sound collector, a synchronizer electrically connected to the data communicator for synchronizing the preprocessed audio data, and a processor electrically connected to the synchronizer for analyzing the synchronized audio data to identify and localize a target audio feature.

Preferably, the multi-mic sound collector includes a carrier and a plurality of sound collecting modules removably attached to the carrier. Each of the sound collecting modules includes one of the plurality of sound receivers, a convertor electrically connected to the sound receiver for converting the sound data into digital audio data; and a microcontroller (MCU) electrically connected to the convertor for controlling sound collection by the sound receiver and preprocessing the digital audio data.

Preferably, the multi-mic sound collector includes a carrier, the plurality of sound receivers removably attached to the carrier, and a preprocessing device. The preprocessing device includes a convertor electrically connected to the sound receivers for converting the sound data into digital audio data; and a MCU electrically connected to the convertor for controlling sound collection by the sound receivers and preprocessing the digital audio data.

Preferably, the processor of the computing device includes a feature extractor for identifying and extracting preliminary audio features from the synchronized audio data, a classifier for separating and classifying the preliminary audio features to obtain the target audio feature, and a signal localizer for analyzing the target audio feature to obtain locational information of a source of the target audio feature.

Preferably, the processor further includes a data analyzer for comparing the obtained target audio feature and the location of the source of the target audio feature with data stored in the computing device to obtain a diagnostic result.

Preferably, the computing device is further in communication with a server for data analysis and storage.

Preferably, the sound receivers are a plurality of stethoscopic chestpieces for auscultating the subject.

Preferably, the amount of the sound receivers are at least three.

Preferably, at least a portion of the sound receivers are arranged rectangularly over a chest of the subject.

Preferably, at least a portion of the sound receivers are arranged rectangularly over a heart of the subject.

Preferably, at least a portion of the sound receivers are arranged triangularly over a heart of the subject.

Preferably, at least a portion of the sound receivers are arranged at left and right costophrenic angles at a posterior chest of the subject.

An embodiment of the present invention provides a sound localization method for the aforementioned sound localization system. The method includes the steps of: acquiring sound data of the subject; identifying a target audio feature from the sound data; and analyzing the target audio feature to obtain locational information of a source of the target audio feature.

Preferably, the step of identifying a target audio feature from the sound data includes the steps of: preprocessing the sound data; extracting preliminary audio features; and separating and classifying the preliminary audio features to obtain the target audio feature.

Preferably, the step of extracting preliminary audio features is performed according to a voice activity detector (VAD) algorithm, a Mel-frequency cepstral coefficient (MFCC) algorithm, and a K-means algorithm.

Preferably, the step of separating and classifying the extracted preliminary audio features includes the steps of: separating noise from the preliminary audio features; classifying normal and abnormal audio features; and separating undesired abnormal audio features to obtain the target audio feature.

Preferably, the step of separating and classifying the extracted preliminary audio features is performed according to a K-nearest neighbor (KNN) algorithm, a Gaussian mixture model (GMM) algorithm, a support vector machine (SVM) algorithm, or a deep neural network (DNN) algorithm.

Preferably, the step of analyzing the target audio feature includes a step of: performing direction of arrival (DOA) estimations on the target audio feature to obtain the locational information of the source of the target audio feature.

Preferably, the sound localization method further includes a step of: comparing the target audio feature and the locational information of the source of the target audio feature with stored data to obtain a diagnostic result.

Preferably, the sound localization method further includes a step of: visualizing the locational information of the source of the target audio feature over a multi-dimensional image of the subject.

In sum, the present invention according to the preferred embodiments couples a multi-mic sound collector with sound analysis and spatial analysis to identify abnormal or pathological sounds coming from a monitored subject and obtain detailed locational information of the source of the abnormal sounds. The present invention facilitates monitoring of the functioning or physiological signs of the subject and allows early detection and diagnosis of abnormalities or diseases.

BRIEF DESCRIPTION OF THE DRAWINGS

The accompanying drawings illustrate one or more embodiments of the present invention and, together with the written description, explain the principles of the present invention. Wherever possible, the same reference numbers are used throughout the drawings to refer to the same or like elements of an embodiment.

In accordance with common practice, the various described features are not drawn to scale and are drawn to emphasize features relevant to the present disclosure. Like reference characters denote like elements throughout the figures and text.

DETAILED DESCRIPTION OF THE PREFERRED EMBODIMENTS

Figure 1:
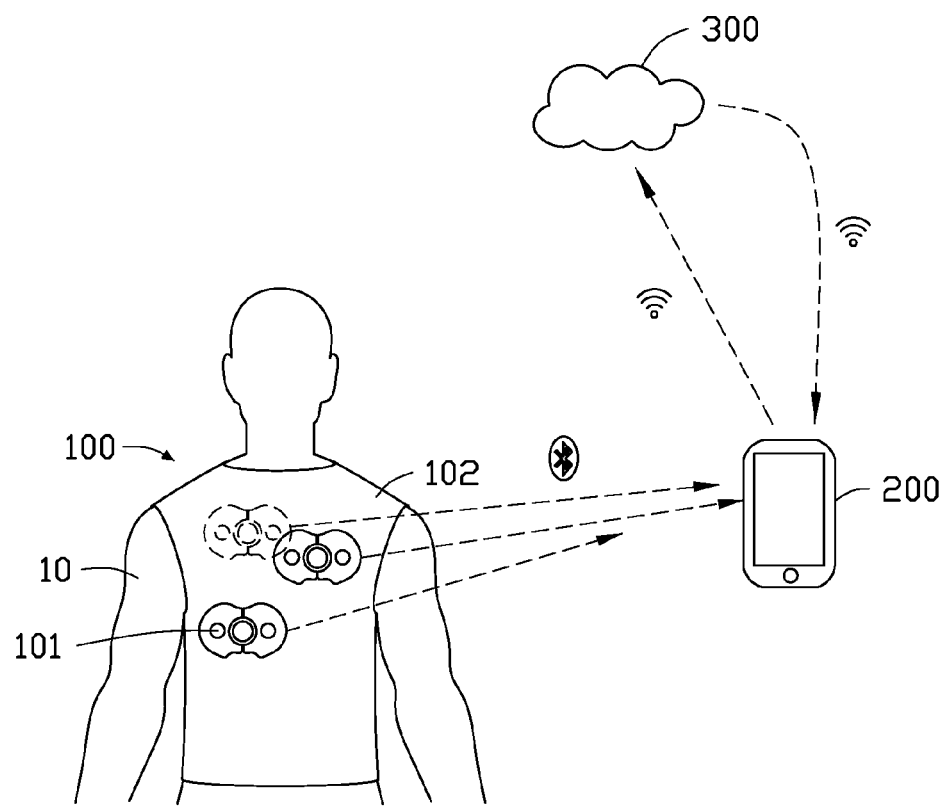
FIG. 1 is a schematic illustration of a sound localization system in accordance with an embodiment of the present invention.

The present invention will now be described more fully hereinafter with reference to the accompanying drawings illustrating various exemplary embodiments of the invention. The present invention may, however, be embodied in many different forms and should not be construed as limited to the embodiments set forth herein. Rather, these embodiments are provided so that this disclosure will be thorough and complete, and will fully convey the scope of the disclosure to those skilled in the art. Like reference numerals refer to like elements throughout.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

It will be understood that the term "and/or" includes any and all combinations of one or more of the associated listed items. It will also be understood that, although the terms first, second, third etc. may be used herein to describe various elements, components, regions, parts and/or sections, these elements, components, regions, parts and/or sections should not be limited by these terms. These terms are only used to distinguish one element, component, region, part or section from another element, component, region, layer or section. Thus, a first element, component, region, part or section discussed below could be termed a second element, component, region, layer or section without departing from the teachings of the present disclosure.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The description will be made as to the embodiments of the present disclosure in conjunction with the accompanying drawings in FIGS. 1 to 11. Reference will be made to the drawing figures to describe the present disclosure in detail, wherein depicted elements are not necessarily shown to scale and wherein like or similar elements are designated by same or similar reference numeral through the several views and same or similar terminology.

Multi-mic sound collector and system and method for sound localization in accordance with various embodiments of the present invention are useful in medical and healthcare environments, such as hospital, healthcare center, etc. Exemplary embodiments may be directed to auscultating live subjects, such as humans, animals, livestock, or other types of living beings. Although examples described herein relate to auscultation over certain areas of a subject's body, for example a chest area, precordia area, abdomen area, extremity area, head area, neck area, or constituent thereof (for example, lung, gastrointestinal system, aorta, tricuspid, brachial artery, femoral artery, trachea, jugular vein, temporal region, mastoid region, etc.), it is not so limited. Those skilled in the art will readily understand that auscultation over other portions of a subject's body may also be advantageously used, depending on the desired information and circumstances. It is therefore appreciated that the disclosed technology may be suitably configured to auscultate over other areas of the subject corresponding to one or more different portion of the body of the subject. Further, some embodiments of the present invention may be optionally configured to obtain a subject's biographical or other identifiable information and associate the information to the aforementioned auscultation performed by a medical or healthcare provider.

Exemplary embodiments of the present invention may also be directed to collection, analysis and localization of sounds generated by non-living objects, such as vehicles, machines, pipelines and the like. Other exemplary embodiments of the present invention may directed to collection and analysis of sounds in a defined space and localization of the sound source within the space.

Referring now to FIG. 1. A sound localization system according to an embodiment of the present invention includes a multi-mic sound collector 100 and a computing device 200. The multi-mic sound collector 100 is configured to collect sounds coming from a subject 10 to be monitored and convert the sounds into audio signals. The computing device 200 is in communication with the multi-mic sound collector 100 and is configured to receive the acoustic signals transmitted from the multi-mic sound collector 100. The computing device 200 may further communicate with a server 300, such as a cloud server.

Figure 2:
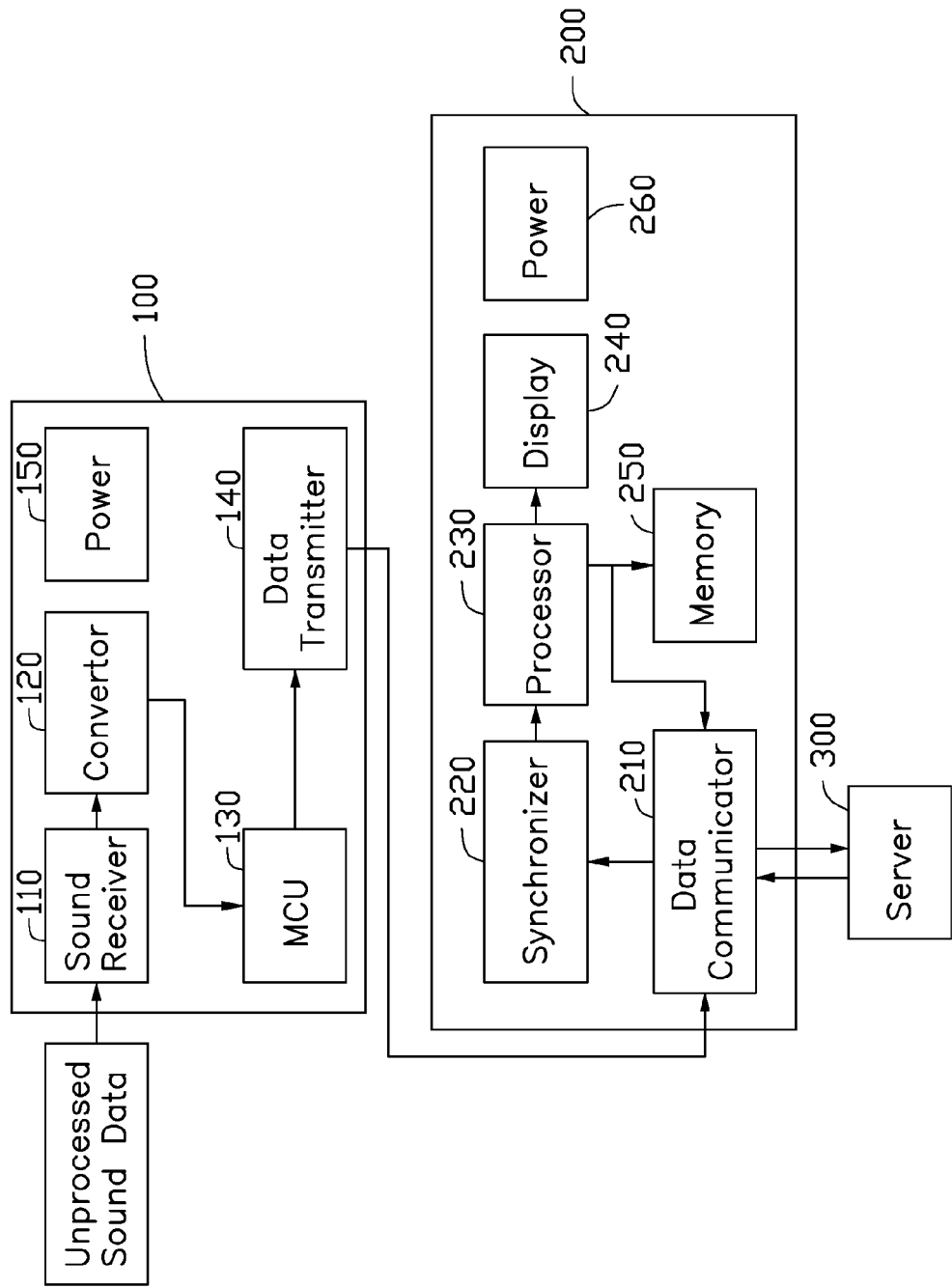
FIG. 2 is a block diagram of a sound localization system in accordance with an embodiment of the present invention.
Figure 3:
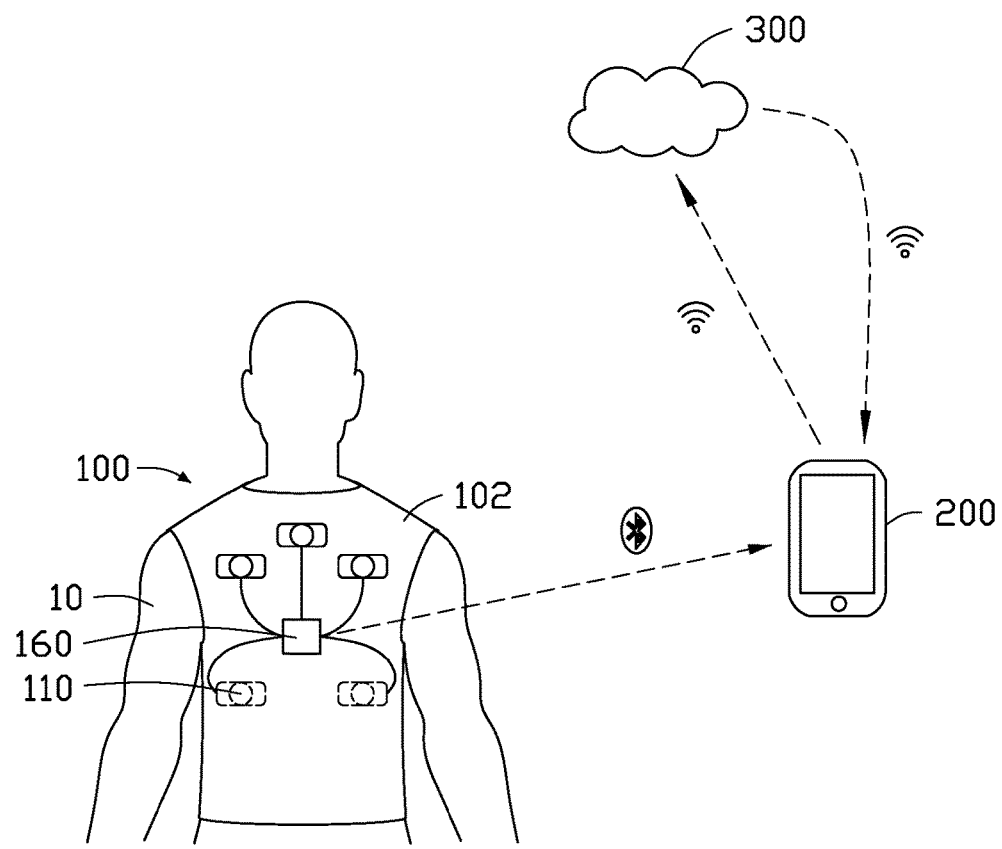
FIG. 3 is a schematic illustration of a sound localization system in accordance with another embodiment of the present invention.
Figure 4A:
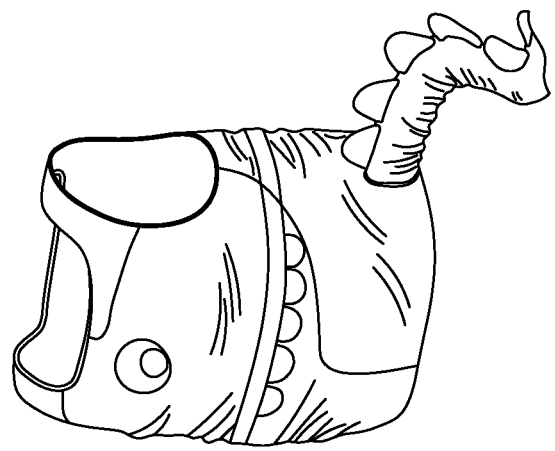
FIGS. 4A-4B are schematic illustrations of carriers of the multi-mic sound collector of the sound localization system in accordance with various embodiments of the invention.
Figure 4A:
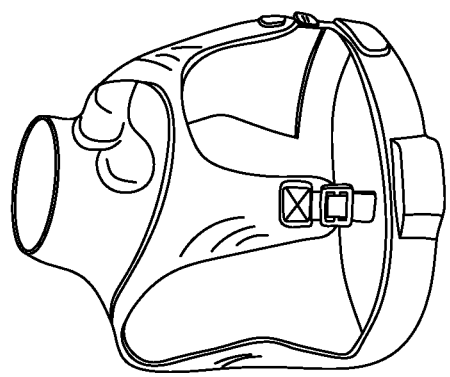
Figure 4A:
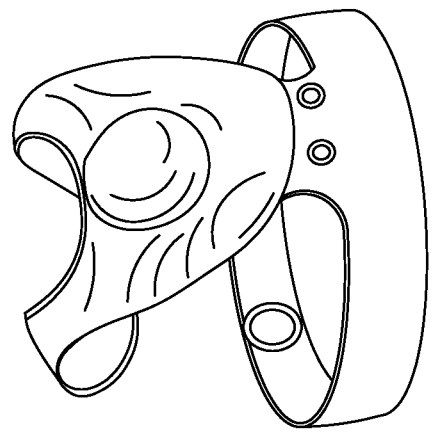
Figure 4B:
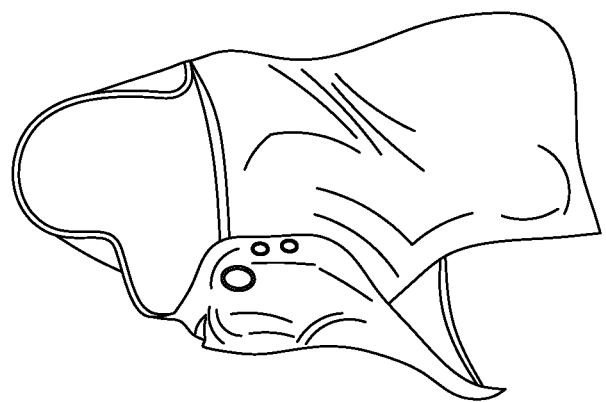
Figure 4B:
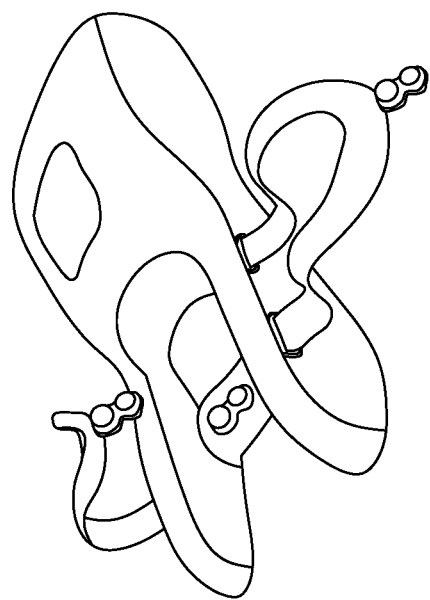

Referring now to FIG. 2. The multi-mic sound collector 100 includes a plurality of sound collecting modules 101 and a carrier 102. Each of the sound collecting modules 101 includes a sound receiver 110, a convertor 120, a microcontroller (MCU) 130, and a data transmitter 140. The sound collecting modules 101 may be suitably placed over an object or a defined space, and the sound receiver 110 may be a microphone configured to collect sounds coming from the object or within the defined space. The sound receiver 110 may also be a stethoscopic chestpiece that are suitably placed over the body of the subject 10 to collect sounds coming internal organs of the subject 10, as exemplarily illustrated in FIG. 1. In an alternative embodiment as illustrated in FIG. 3, the multi-mic sound collector 100 may include a plurality of the sound receivers 110, a preprocessing device 160, and the carrier 102. The convertor 120, the microcontroller (MCU) 130, and the data transmitter 140 are integrated into the preprocessing device 160.

It is to be understood that the sound receivers 110 are not limited to the aforementioned microphones or stethoscopic chestpieces, but may be micro-electromechanical (MEMS) microphones, condenser microphones, electret condenser microphones, capacitive microphones, piezoelectric microphones, or any sound receivers that can or can be configured to collect audible sounds and/or inaudible sounds, such as ultrasonic and hypersonic sounds, or any sensors that can or can be configured to detect mechanical vibration in various frequencies and to convert the vibration into electrical signals. In addition, the sound receivers 110 of the sound collectors 101 may be identical, or be a combination of different types of sound receivers. For higher precision in sound localization, the multi-mic sound collector 100 preferably includes three or more sound receivers 110 that are not all arranged on a same plane.

Further, the sound receivers 110 may have frequency response suitable for medical use. For example, power attenuation of the sound receivers 110 may be less than 12 dB in the frequency range of 100-500 Hz and less than 20 dB in the frequency range of 500-1000 Hz. Frequency response of the sound receivers 110 may be adjusted for different applications, such as detection of heart sounds or breath sounds. In general, frequency response of the sound receivers 110 may be optimized to 20-800 Hz for heart sound detection, 20-100 Hz for detection of the first to fourth heart sounds, 20-00 Hz or 100-600 Hz for detection of heart murmurs. Similarly, frequency response of the sound receivers 110 may be optimized to 200-600 Hz for detection of vesicular breath sounds, and to 20-100 Hz for detection of bronchial breath sounds.

The sound receivers 110 are removably attached to the carrier 102 for continuous monitoring of a subject. As exemplarily illustrated in FIG. 4A, the carrier 102 may be, but is not limited to, a vest, shirt, jacket, suspenders, overall, shortall, sleeve, waistband, or other types of outfit. Alternatively, as exemplified in FIG. 4B, the carrier 102 may be a common consumer product, such as a pillow, bath towel, sleep bag, backpack, or car seat. It is to be understood that the carrier 102 may have a variety of designs for specific applications or user populations; for example, the carrier may have animal-themed designs for young children or may be integrated with other technical features for more comfort, convenience, or diversified functions.

Figure 5A:
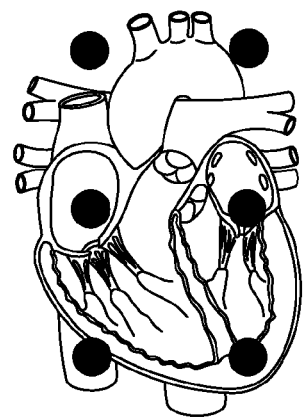
FIGS. 5A-5C are schematic illustrations of the arrangement of the sound receivers of the multi-mic sound collector in accordance with various embodiments of the invention.
Figure 5B:
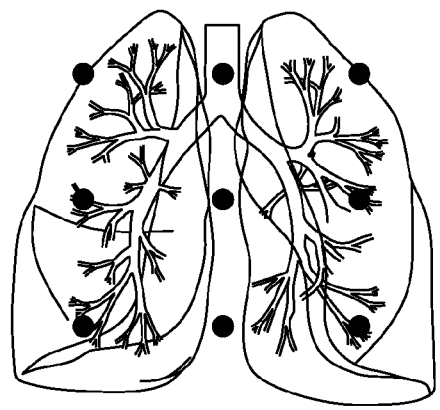
Figure 5C:
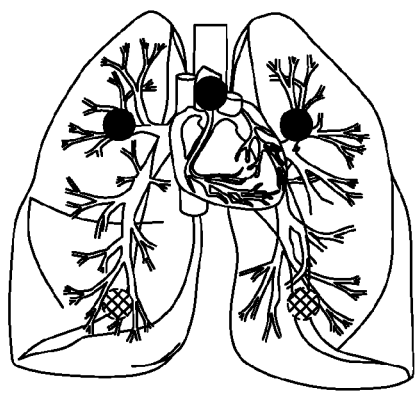

The amount and arrangement of the sound receivers 110 on the carrier 102 may vary according to different applications. For example, to monitor heart sound and bronchial breath sound of an adult patient, six stethoscopic chestpieces, as illustrated by dark full circles in FIG. 5A, are preferably arranged rectangularly over the heart region at the anterior chest, with each of the chestpieces being spaced apart from the adjacent ones by a distance (for example, 5 cm). Meanwhile, to monitor sound of the entire lung field of the adult patient, nine stethoscopic chestpieces, as illustrated by dark full circles in FIG. 5B, are preferably arranged rectangularly at the posterior chest, with each of the chestpieces being spaced apart from the adjacent ones by a distance (for example, 10 cm). In contrast, as illustrated in FIG. 5C, to monitor a young child, three stethoscopic chestpieces are preferably arranged triangularly at a higher region at the anterior chest, with each of the chestpieces being spaced apart from the adjacent ones by a distance (for example, 5 cm) to record sounds of the heart and upper part of the lung; meanwhile, two stethoscopic chestpieces, as illustrated by patterned circles in FIG. 5C, are arranged at the left and right costophrenic angles at the posterior chest and spaced apart by a distance (for example, 10 cm) to record sounds of the lower part of the lung of the young child. It is to be understood that the preferred embodiments illustrated in FIGS. 5A-5C are merely exemplary, and that the present invention does not limit the amount and arrangement of the sound receivers to those exemplified in the drawings.

Referring again to FIG. 2. The convertor 120 of the multi-mic sound collector 100 is electrically connected to the plurality of sound receivers and is configured to convert and encode the acquired unprocessed sound data from analog audio data into digital audio data. The MCU 130 is electrically connected to the convertor 120 and is configured to control sound collection of the sound receiver 110 and preprocess, such as down sampling, positioning, tagging, augmenting, filtering, and time stamping, the audio data received from the convertor 120. The data transmitter 140 is electrically connected to the MCU 130 and is configured to transmit preprocessed audio data to the computing device 200. The multi-mic sound collector 100 may further include a power 150 to provide and store electricity for the multi-mic sound collector 100. The power 150 may be a rechargeable or non-rechargeable battery. In the case of rechargeable battery, the multi-mic sound collector 100 may further include a charging port (not shown) for charging the rechargeable battery. Alternatively, the multi-mic sound collector 100 may further include a wireless charging circuit to be coupled to a wireless charging dock.

The computing device 200 includes a data communicator 210, a synchronizer 220, a processor 230, a display 240, a memory 250. The data communicator 210 is in communication with the data transmitter 140 of the multi-mic sound collector 100 and is configured to receive preprocessed audio data from the multi-mic sound collector 100. The synchronizer 220 is electrically connected to the data communicator 210 and is configured to synchronize the received preprocessed audio data. The processor 230 is electrically connected to the synchronizer 220 and is configured to analyze the synchronized data to identify and localize abnormal sounds. The processor 230 is further electrically connected to the display 240 for data presentation and visualization, the data communicator 210 for data communication with other device(s), and the memory 250 for data storage. The display 240 may be a LCD screen, touch panel, OLED, CRT, projector, or other types of display components. The memory 260 may be volatile memory or non-volatile memory, such as RAM, ROM, EEPROM, flash memory, optical storage, magnetic disk storage or other magnetic storage devices. The data communicator 210 may further communicate with the server 300 for more data analysis and storage. It is to be understood that the embodiments of the present invention provided herein do not limit the hardware in which data processing and analyses take place; that is, some of the functions performed by the processor of the computing device 200 may be executed by the server 300, and vice versa. The computing device 200 may further include a power 260 to provide and store electricity for the computing device 200.

The computing device 200 may be, but is not limited to, a smartphone, a mobile device, a tablet computer, a notebook computer, a desktop computer or a work station. In a preferred embodiment, the computing device 200 is a smartphone capable of receiving Bluetooth signals from the multi-mic sound collector 100. It is to be understood that data transmission and communication among the multi-mic sound collector 100, the computing device 200, and the server 300 may be performed via USB, micro USB, serial port, IEEE1394, Bluetooth, Wi-Fi, Infrared, ZigBee, WiMAX, 3G, 4G, 4G LTE, 5G, or any other commonly known wired or wireless transmission means.

Figure 6:
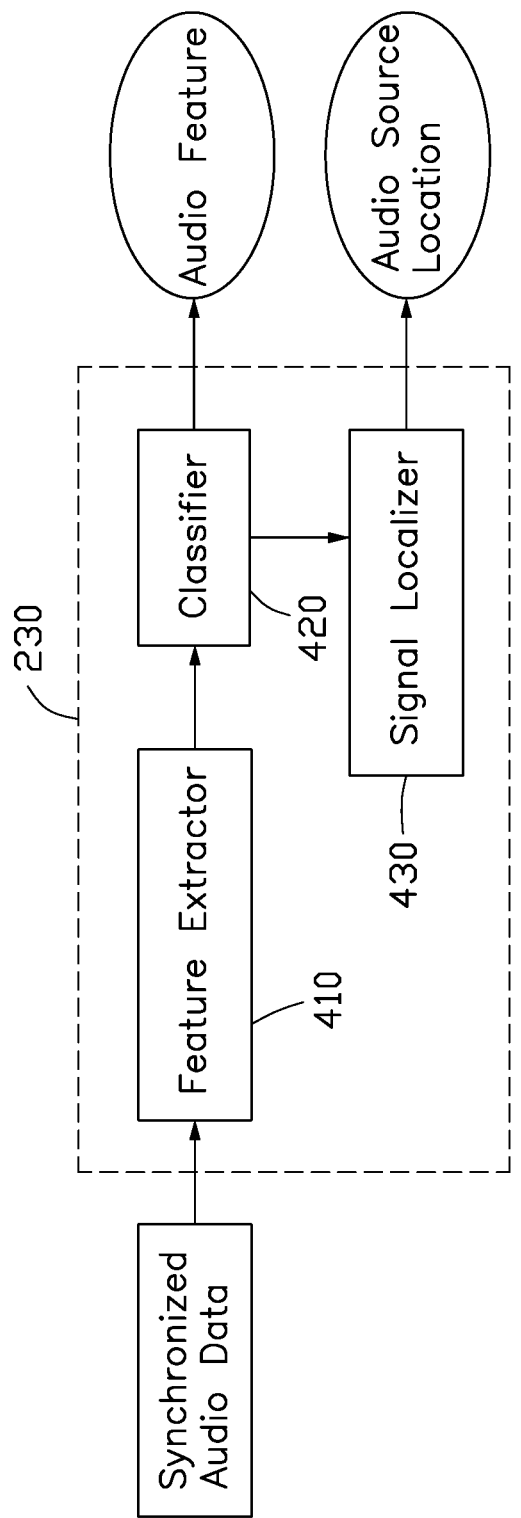
FIG. 6 is a block diagram of a processor of a computing device of a sound localization system in accordance with an embodiment of the present invention.

Referring now to FIG. 6. The processor 230 of the computing device 200 includes a feature extractor 410, a classifier 420, and a signal localizer 430. The feature extraction module 410 is configured to identify and extract preliminary audio features from the synchronized audio data received from the synchronizer 220. The classifier 420 is configured to separate and classify the extracted preliminary audio features received from the feature extractor 410 to single out a target audio feature. The signal localizer 430 is configured to analyze the target audio feature obtained by the classifier 420 by performing direction of arrival (DOA) estimations, such as multiple signal classification (MUSIC), beamforming and other data processing algorithms, to obtain locational information of the source of the target audio feature. The MUSIC algorithm may include the group delay MUSIC (GD-MUSIC), recursively applied and projected MUSIC, minimum variance distortionless response (MVDR), and linear constraint minimum variance (LCMV) algorithms. The beamforming algorithm may include the generalized sidelobe canceller (GSC) algorithm. The processor 230 may be an Intel Core i7 processor, ARM processor, x8086 or other processor or application specific integrated circuit having similar computing capability.

The processor 230 may further include a data analyzer (not shown in figure) configured to compare the obtained target audio feature and audio source location with previous audio record of the subject 10, audio data of healthy or normal subjects, or default settings stored in the memory 250 to obtain a diagnostic result. For example, mid-to-late systolic heart murmur detected at the upper left part of the heart could indicate mitral valve prolapse (MVP).

Figure 7:
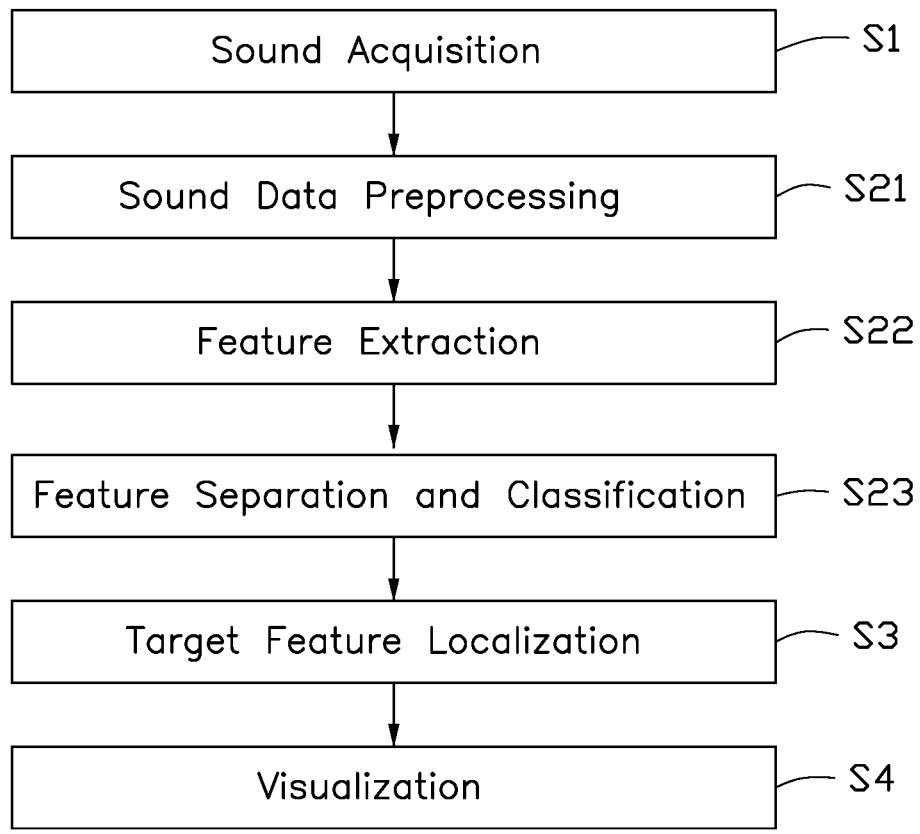
FIG. 7 is a flow diagram showing the steps of a sound localization method in accordance with an embodiment of the present invention.

Referring now to FIG. 7. According to various embodiments of the present invention, sound localization method of the sound localization system includes the steps of: (S1) acquiring sound data of a subject; (S2) identifying a target audio feature from the sound data; and (S3) analyzing the target audio feature to obtain the locational information of the source of the target audio feature.

Acquisition of sound data as in Step S1 is performed by the multi-mic sound collector 100 of the sound localization system of the aforementioned embodiments to collect sounds coming from a subject or object or from a defined space.

In an embodiment, identification of a target audio feature from the sound data as in Step S2 includes the steps of: (S21) preprocessing the sound data; (S22) extracting preliminary audio features; and (S23) separating and classifying the preliminary audio features to obtain the target audio feature. Preprocessing of the sound data as in Step S21 includes the steps of: (S211) converting and encoding the acquired sound data into digital audio data; (S212) preprocessing the digital audio data; and (S213) synchronizing the audio data. Processing of the digital audio data as in Step S212 includes as down sampling, positioning, tagging, augmenting, filtering, and time stamping of the digital audio data.

In an embodiment, extraction of preliminary audio features as in Step S22 is performed by processing the synchronized audio data according to the voice activity detector (VAD), Mel-frequency cepstral coefficient (MFCC), and K-means algorithms. In an embodiment, separation and classification of the extracted preliminary audio features as in Step S23 may include the steps of: (S231) separating noise from the preliminary audio features; (S232) classifying normal and abnormal audio features; and (S233) separating undesired abnormal audio features to obtain a target audio feature; and are performed according to the K-nearest neighbor (KNN), Gaussian mixture model (GMM), support vector machine (SVM), or deep neural network (DNN) algorithm. In an exemplary embodiment where the sound receivers 110 of the multi-mic sound collector 100 are stethoscopic chestpieces that are optimized for detecting heart sounds, more than one abnormal audio features may be detected from the acquired heart sounds. When the $4^{th}$ heart sound is the target sound feature (or the sound of interest), Step S233 would be performed to eliminate abnormal audio features that are not associated with the $4^{th}$ heart sound, thereby singling out the target audio feature (eg. the $4^{th}$ heart sound as in this example) for further analysis.

The step of analyzing the target audio feature as in Step S3 includes the step of: (S31) defining coordinates of the sound receivers 110; and (S32) performing direction of arrival (DOA) estimations on the target audio feature to obtain the locational information of the source of the target audio feature. The DOA estimation may include multiple signal classification (MUSIC), such as GD-MUSIC, recursively applied and projected MUSIC, MVDR, and LCMV algorithms, beamforming, such as GSC algorithm, and other data processing algorithms. Step S3 may further include the step of: (S33) comparing the target audio feature and the locational information of the source of the target audio feature with stored data to obtain a diagnostic result. The stored data may be previous audio record of the subject, audio data of healthy or normal subjects, or default settings stored in the system.

The sound localization method may further include the step of: (S4) visualizing the locational information of the source of the target audio feature. The locational information may be visualized on a coordinate system defined by positions of the sound receivers 110 or over an uni- or multi-dimensional virtual image or model of the subject so as to provide a more intuitive diagnostic result. The model may be an anatomical model reconstructed from a photo image, an X-ray image, computed tomographic image, or magnetic resonance image. Alternatively, the anatomical model may be a template model established from an anatomical atlas of the body, such as the chest region, head and neck region, and abdominal region.

Figure 8A:
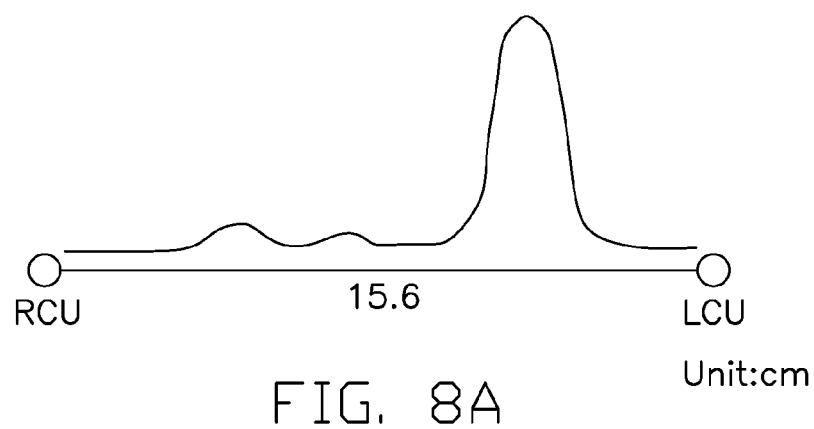
FIGS. 8A-8C are schematic illustrations of the results of spatial analysis in accordance with various embodiments of the present invention.
Figure 8B:
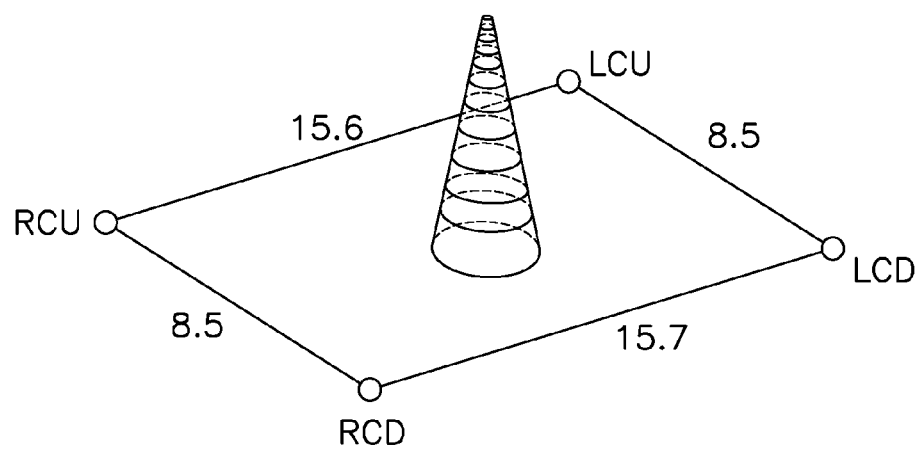
Figure 8C:
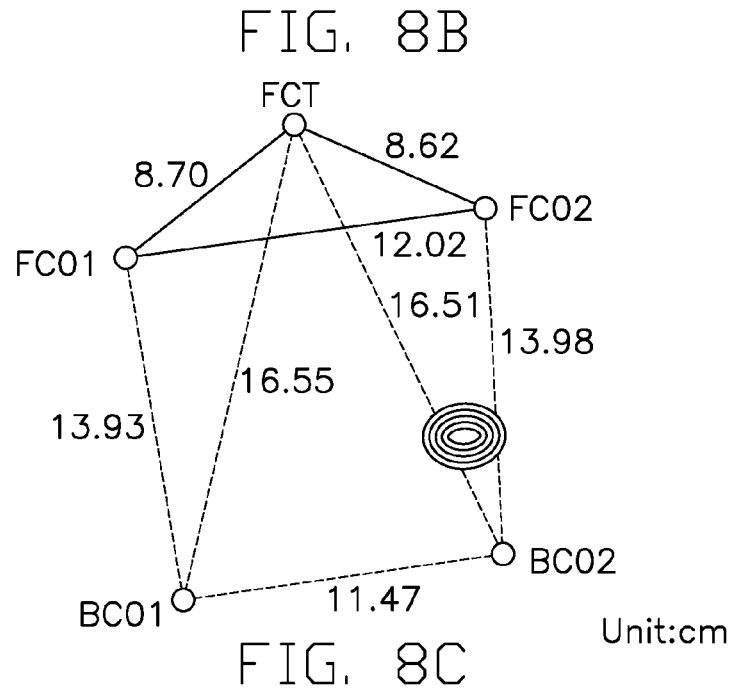

According to some exemplary embodiments, the location of an abnormal sound may be visualized one-dimensionally between the right chest up (RCU) and left chest up (LCU) spots, as illustrated in FIG. 8A, or two-dimensionally on a plane defined by the right chest down (RCD), left chest down (LCD), RCU, and LCU spots, as illustrated in FIG. 8B, or more preferably three-dimensionally in a space defined by the anterior chest thymus (FCT), anterior chest (FC) and posterior chest (BC) spots, as illustrated in FIG. 8C.

Figure 9A:
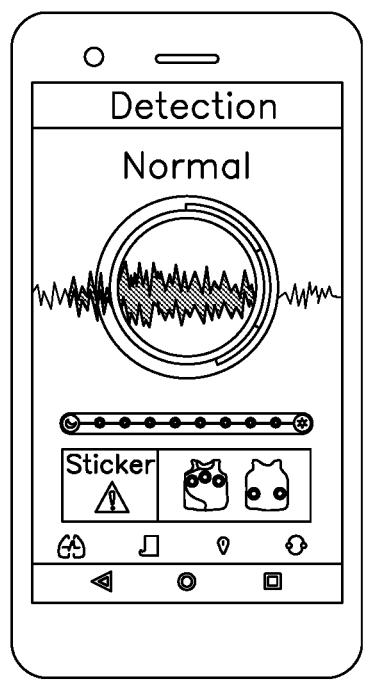
FIGS. 9A-9B are schematic illustrations of the user interface of an application in the computing device of the sound localization system in accordance with an embodiment of the present invention.
Figure 9B:
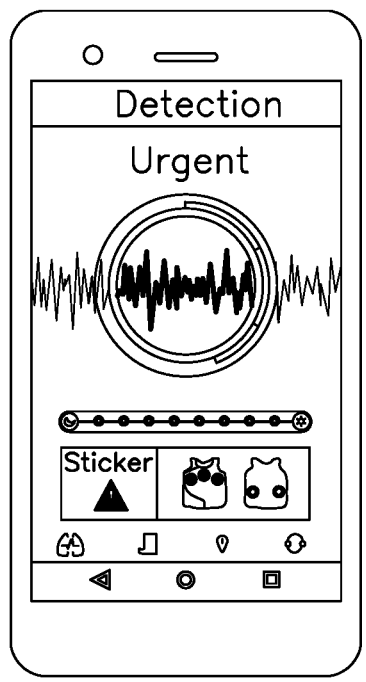

As exemplified in FIGS. 9A and 9B, the diagnostic result may also be visualized by an application on the computing device 200. For example, as illustrated in FIG. 9A, the application may show the recorded soundwaves and sound intensity and frequency, illustrate the locations of the sound receivers, and indicate the diagnostic result (such as the physiological condition of the subject). When abnormal sound occurs, as illustrated in FIG. 9B, the application may present an alert message and indicate the locations at which the abnormal sound is detected.

The sound localization method may further include the step of: (S5) recording and storing data associated the target audio feature. The data may include type, frequency, intensity and location of the audio feature, as well as chronological changes in frequency, intensity, and location of the audio feature.

Figure 10:
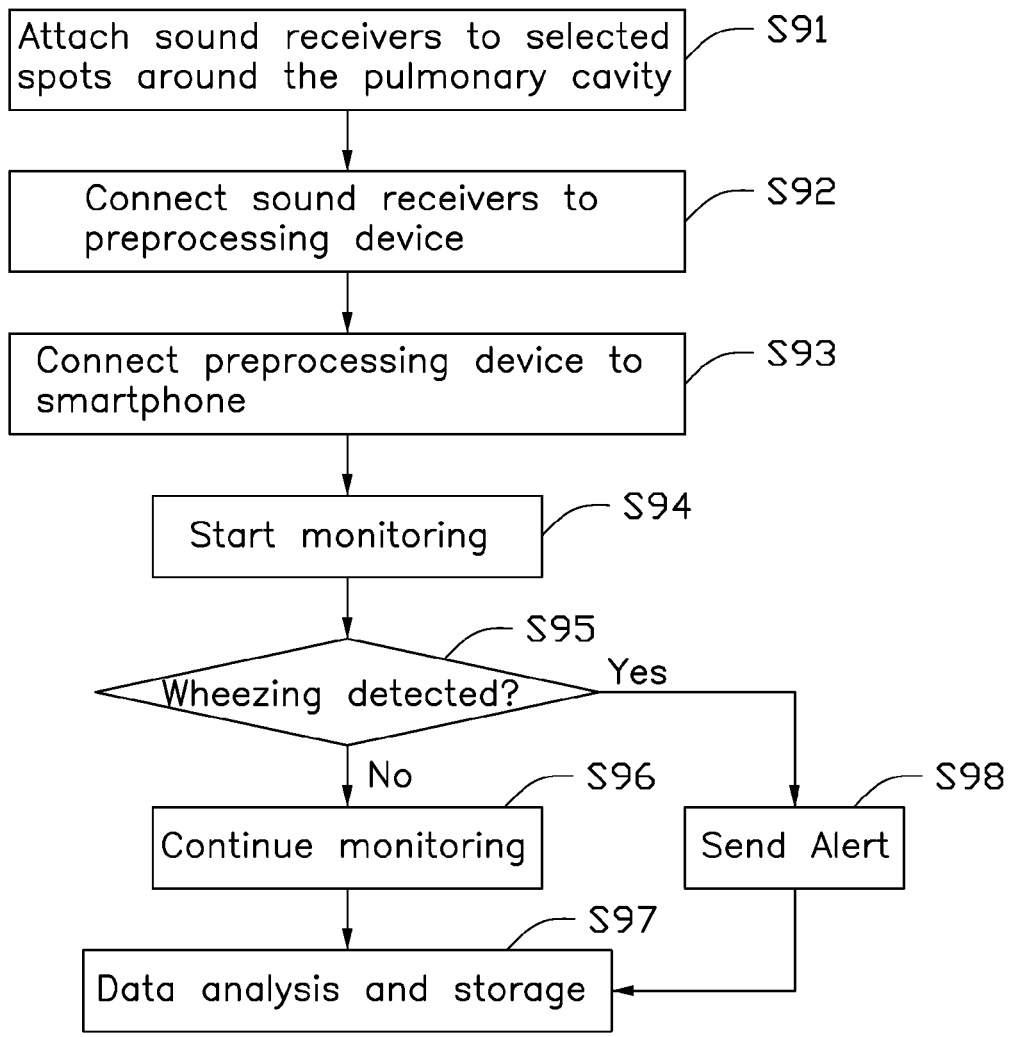
FIG. 10 is a flow diagram showing the steps of breathing sound monitoring and analysis in accordance with an exemplary embodiment of the present invention.

Referring now to FIG. 10. The sound localization system according to an exemplary embodiment of the present invention may be applied to monitoring of breathing sound and detection asthmatic symptoms. In the example, sound receivers of the sound collector are stethoscopic chestpieces integrated in the form of patches, which are removably attached to five selected spots of a patient (S91); as illustrated in FIG. 3, the spots may be the right and left upper lobes of the lung region at anterior chest, right and left lower lobes of the lung region at posterior chest, and the bronchial region. After the sound receiving patches are attached to the patient, the patches are connected to a preprocessing device (S92); the preprocessing device includes a MCU that is configured to initiate a sound collection (or auscultation) routine by the patches periodically for a default duration of time. The preprocessing device is switched on and coupled to a smartphone via Bluetooth (S93). The user may set from an application installed on the smartphone the time, duration and items for monitoring, as well as the type of alert sent in case of detection of abnormal events, and start the monitoring program (S94).

Once started, the MCU initiates a sound collection routine (eg. sequential auscultation by the five sound receiving patches) every ten minutes and wirelessly transmits the audio data to the smartphone for algorithmic analyses of the data to identify a target audio feature, such as wheezing, or other pathological sound features (S95). When no abnormality is detected, the MCU would continue the auscultation routine until the set duration of monitoring ends (S96); thereafter, all of the collected audio data is wirelessly transmitted to a cloud server for storage and trend analysis (S97); further, the monitoring record and analysis results in the server may be transmitted back to the smartphone for detailed diagnosis and follow-ups by the user or physicians. Alternatively, when wheezing is detected, the smartphone application would issue an alert ringtone and/or message and indicate treatment advices (S98); meanwhile, the MCU stops the periodic auscultation routine and performs continuous auscultation until the alert is canceled.

Figure 11:
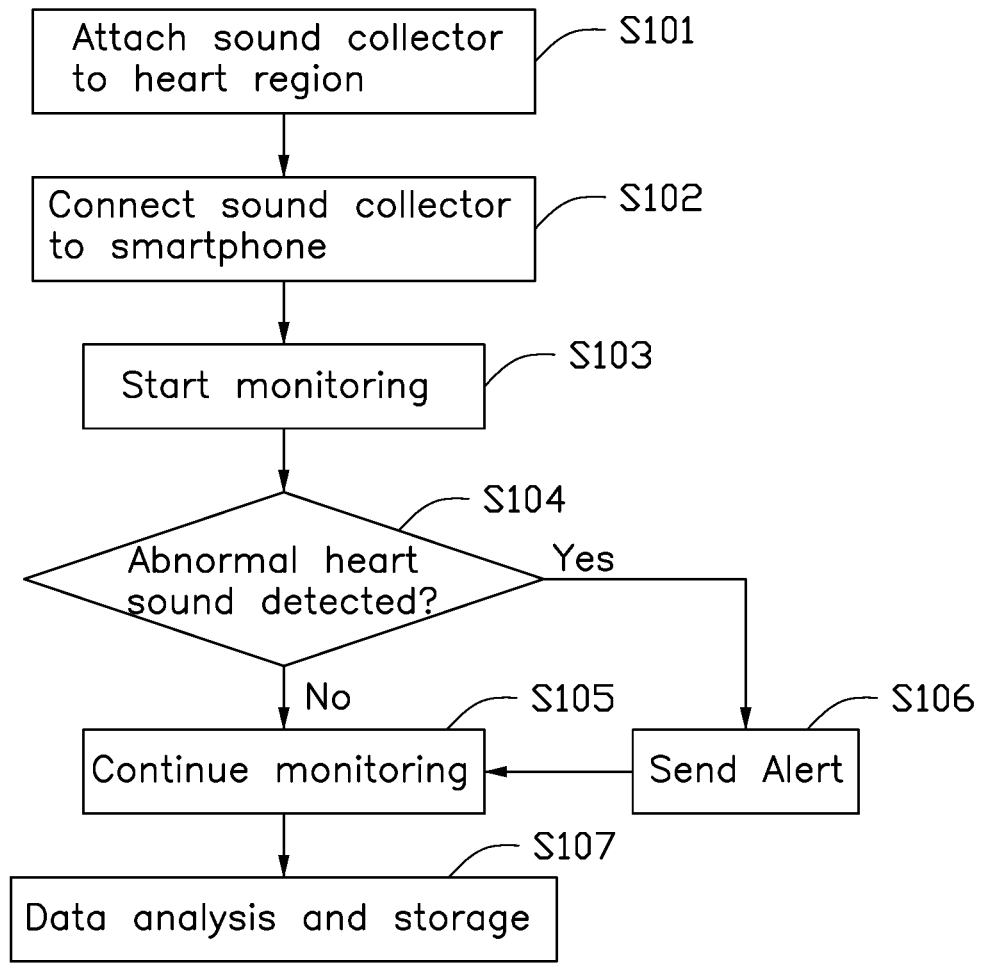
FIG. 11 is a flow diagram showing the steps of breathing sound monitoring and analysis in accordance with an exemplary embodiment of the present invention.

Likewise, as illustrated in to FIG. 11. The sound localization system according to an exemplary embodiment of the present invention may be applied to monitoring of heart sound and detection arrhythmic symptoms. In the example, sound collectors are in the form of patches, each of which includes a stethoscopic chestpiece and a MCU, as illustrated in FIG. 1. Two sound collecting patches are removably attached to the heart region at front and posterior chest of a user (S101). The MCU is configured to initiate recording of heart sound and heart rate by the stethoscopic chestpiece. After the sound collecting patches are attached to the user, the patches are switched on and coupled to a smartphone via Bluetooth (S102). The user may confirm from the application installed on the smartphone status of connection between the patches and the smartphone and check audio features of the detected heart sound, heart rate, and calculated heart rate variability under an active mode. The user may also switch the system to a standby mode from the application; the MCUs of the sound collecting patches would stop heart sound and heart rate recording under the standby mode.

When experiencing irregular heartbeat or chest pain, the user may switch the system back to the active mode from the application, and activate recording of heart sound and heart rate by the sound collecting patches (S103). When abnormal heart sound or heart rate is not detected (S104), the sound collecting patches would start a auscultation routine (eg. continuous sound collection and recording for three minutes) and return to the standby mode (S105). Alternatively, when abnormal heart sound or heart rate is detected (S104), the smartphone application would issue an alert ringtone and/or message and indicate treatment advices to the user (S106); the smartphone may also send a notification of such event to a designated hospital or medical institution for necessary emergency responses. Meanwhile, the sound collecting patches would repeat the auscultation routine (S105) and return to the standby mode only until the heart rate recovers. All of the collected auscultation data is wirelessly transmitted to a cloud server for storage and trend analysis (S107); the monitoring record and analysis results in the server may be transmitted back to the smartphone for detailed diagnosis and follow-ups by the user or physicians.

In sum, the present invention according to the preferred embodiments couples a multi-mic sound collector with sound analysis and spatial analysis to identify abnormal or pathological sounds coming from a monitored subject and obtain detailed locational information of the source of the abnormal sounds. The present invention facilitates monitoring of the functioning or physiological signs of the subject and allows early detection and diagnosis of abnormalities or diseases.

Previous descriptions are only embodiments of the present disclosure and are not intended to limit the scope of the present disclosure. Many variations and modifications according to the claims and specification of the disclosure are still within the scope of the claimed disclosure. In addition, each of the embodiments and claims does not have to achieve all the advantages or characteristics disclosed. Moreover, the abstract and the title only serve to facilitate searching patent documents and are not intended in any way to limit the scope of the claimed disclosure.

What is claimed is:

1. A sound localization system, comprising:
    a multi-relic sound collector comprising a plurality of sound receivers for collecting sound data of a subject; and
    a computing device in communication with the multi-mic sound collector, comprising:
        a data communicator for receiving preprocessed audio data from the multi-mic sound collector;
        a synchronizer electrically connected to the data communicator for synchronizing the preprocessed audio data; and
        a processor electrically connected to the synchronizer for analyzing the synchronized audio data to identify and localize a target audio feature, and comprising a feature extractor for identifying and extracting preliminary audio features from the synchronized audio data according to a voice activity detector (VAD) algorithm, a Mel-frequency cepstral coefficient (MFCC) algorithm, and a K-means algorithm, sequentially.

2. The sound localization system according to claim 1, wherein the multi-mic sound collector comprises:
    a carrier; and
    a plurality of sound collecting modules removably attached to the carrier, each of the sound collecting modules comprising:
        one of the plurality of sound receivers;
        a convertor electrically connected to the sound receiver for converting the sound data into digital audio data; and
        a microcontroller (MCU) electrically connected to the convertor for controlling sound collection by the sound receiver and preprocessing the digital audio data.

3. The sound localization system according to claim 1, wherein the multi-mic sound collector comprises:
    a carrier;
    the plurality of sound receivers removably attached to the carrier; and
    a preprocessing device, comprising:
        a convertor electrically connected to the sound receivers for converting the sound data into digital audio data; and
        a microcontroller (MCU) electrically connected to the convertor for controlling sound collection by the sound receivers and preprocessing the digital audio data.

4. The sound localization system according to claim 1, wherein the processor of the computing device comprises:
    a classifier for separating and classifying the preliminary audio features to obtain the target audio feature; and
    a signal localizer for analyzing the target audio feature to obtain locational information of a source of the target audio feature.

5. The sound localization system according to claim 4, wherein the processor further comprises:
    a data analyzer for comparing the obtained target audio feature and the location of the source of the target audio feature with data stored in the computing device to obtain a diagnostic result.

6. The sound localization system according to claim 1, wherein the computing device is further in communication with a server for data analysis and storage.

7. The sound localization system according to claim 1, wherein the sound receivers are a plurality of stethoscopic chestpieces for auscultating the subject.

8. The sound localization system according to claim 1, wherein an amount of the sound receivers are at least three.

9. The sound localization system according to claim 1, wherein at least a portion of the sound receivers are arranged rectangularly over a chest of the subject.

10. The sound localization system according to claim 1, wherein at least a portion of the sound receivers are arranged rectangularly over a heart of the subject.

11. The sound localization system according to claim 1, wherein at least a portion of the sound receivers are arranged triangularly over a heart of the subject.

12. The sound localization system according to claim 1, wherein at least a portion of the sound receivers are arranged at left and right costophrenic angles at a posterior chest of the subject.

13. A sound localization method for a sound localization system comprising a plurality of sound receivers for collecting sound data of a subject and a computing device in communication with the sound receivers, comprising steps of:
    acquiring sound data of the subject;
    identifying a target audio feature from the sound data; and
    analyzing the target audio feature to obtain locational information of a source of the target audio feature;
    wherein the step of identifying a target audio feature from the sound data comprising steps of:
        preprocessing the sound data;
        extracting preliminary audio features according to a voice activity detector (VAD) algorithm, a Mel-frequency cepstral coefficient (MFCC) algorithm, and a K-means algorithm, sequentially; and
        separating and classifying the preliminary audio features to obtain the target audio feature.

14. The sound localization method according to claim 13, the step of separating and classifying the extracted preliminary audio features comprising steps of:
    separating noise from the preliminary audio features;
    classifying normal and abnormal audio features; and
    separating undesired abnormal audio features to obtain the target audio feature.

15. The sound localization method according to claim 13, the step of separating and classifying the extracted preliminary audio features is performed according to a K-nearest neighbor (KNN) algorithm, a Gaussian mixture model (GMM) algorithm, a support vector machine (SVM) algorithm, or a deep neural network (DNN) algorithm.

16. The sound localization method according to claim 13, the step of analyzing the target audio feature comprising a step of:
    performing direction of arrival (DOA) estimations on the target audio feature to obtain the locational information of the source of the target audio feature.

17. The sound localization method according to claim 13, further comprising a step of:
- comparing the target audio feature and the locational information of the source of the target audio feature with stored data to obtain a diagnostic result.

18. The sound localization method according to claim 13, further comprising a step of:
- visualizing the locational information of the source of the target audio feature over a multi-dimensional image of the subject.

* * * * *